United States Patent [19]
Reichau et al.

[11] Patent Number: 5,728,937
[45] Date of Patent: Mar. 17, 1998

[54] ARRANGEMENT FOR TESTING THE MATERIAL OF FORMED PARTS

[75] Inventors: Ralf Reichau, Berlin, Germany; Claudio Cavalloni, Regensdorf, Switzerland; Andreas Kirchheim, Hettlingen, Switzerland; Peter Wolfer, Kleinandelfingen, Switzerland

[73] Assignee: K. K. Holding AG, Winterthur, Switzerland

[21] Appl. No.: 712,200

[22] Filed: Sep. 11, 1996

[30] Foreign Application Priority Data

Sep. 15, 1995 [CH] Switzerland ............ 02602/95

[51] Int. Cl.$^6$ .................................................. G01M 7/02
[52] U.S. Cl. ............................................................ 73/579
[58] Field of Search ...................... 73/579, 582, 588, 73/573, 574, 575, 632, 661; 72/17.3; 425/135

[56] References Cited

U.S. PATENT DOCUMENTS

| | | | |
|---|---|---|---|
| 3,307,393 | 3/1967 | Kessler | 73/584 |
| 4,479,386 | 10/1984 | Beggs et al. | 73/582 |
| 4,519,245 | 5/1985 | Evvans | 73/573 |
| 5,365,457 | 11/1994 | Madigosky | 73/573 |

OTHER PUBLICATIONS

P. Highmore et al., "Resonance Methods," in *Ultrasonic Testing*, J. Szilard (ed.), 1982, John Wiley & Sons Ltd.

Development of Piezo–Electric Actuators and Sensors for Electronically Controlled Suspension, JSAE Review, (Jap. Soc. Of Automotive Engineers), vol. 12, pp. 48–52, Jul, 1991.

*Primary Examiner*—John E. Chapman

[57] ABSTRACT

For a comparative material testing of similar formed parts based on their dynamic behaviour under acoustic excitation vibrations, in order to obtain clear-cut information about the material properties it is necessary to assure constant excitations of the vibration generator and a constant pressing force when coupling this to the object being tested. This is accomplished by using a piezoelectric actuator in an assembly unit with an electromechanical sensor and a coupling element, whereby the excitation voltages of the actuator are monitored and its vibrations passing into the formed part are registered by the sensor.

16 Claims, 4 Drawing Sheets

ARRANGEMENT FOR TESTING THE MATERIAL OF FORMED PARTS

BACKGROUND AND SUMMARY OF THE INVENTION

The invention relates to an arrangement for testing the material of formed parts to detect defects and properties using frequency spectrum of mechanical excitation vibrations and more specifically, to assuring the accurate operation of the actuator.

In the production technology for formed parts of typically sheet metal or plastic, there is often the problem of detecting immediately after the [production] formation process within the short time between two processing stations in a production line for instance, parts of defective composition or parts that have been damaged in the course of forming, and rejecting them from the further production process.

It is known that "sound" and defective formed parts differ in their dynamic behaviour under acoustic vibrations, in their stiffness and damping capacity for example. On this basis it has been proposed (EP application 951166396 of 23rd Oct. 1995) to determine such differing response by measuring the acoustic vibrations excited by a vibration generator and introduced into the formed part, and sorting the parts accordingly. In implementing a process of this kind, for example the acoustic vibration spectrum of a "sound", i.e. defect-free part, or one with defects only within a tolerance range is taken as reference spectrum, with which the spectrum of the other parts is compared. Deviations in the spectrums of the test parts that exceed the tolerance limit are used to reject the parts in question.

The purpose of the invention is to provide a suitable arrangement for the testing process described, ensuring in particular that both the excitation of the vibration generator in shape and amplitude and its acoustic coupling for reference and test parts are equal and constant, since only with constant excitation and coupling do the measured and recorded spectrums give a clear and unambiguous statement on the state of the material of the formed parts tested.

These objects are achieved as follows:

An actuator/sensor arrangement on piezoelectric/electromechanical basis, as known for example from the shock absorbers in automobile engineering (Akira FUKAMI et al., Development of Piezo-Electric Actuators and Sensors for Electronically Controlled Suspension, JSAE Review, Jap. Soc. Of Automotive Engineers, Vol 12, No. 3 [1991], pp. 48–52), is suitable for combination with a coupling element as a compact and robust excitation and measuring device for the testing process described, its measuring signals being analyzed in simple manner in the signal analyzer and made available for further use.

An equal and constant excitation is ensured for all formed parts by the means for detecting the signal of the generator. The generator generates either single pulses or vibrations variable over a certain frequency range, e.g. sinusoidal vibrations of constant shape and amplitude as excitation signals for the actuator. This detection may consist for example of a program for supplying single voltage pulses of a certain amplitude for each frequency. This means may consist also of measuring the excitation of the actuator and correcting it appropriately, or possibly keeping it to a constant value of shape and amplitude in a control loop.

Constant coupling may be obtained for example by a spring force, a hydraulic or pneumatic pressing force, or the pressure of a weight, such as a robot arm. Advantageous, however, is the provision of means triggering excitation of the actuator only after an adjustable threshold is exceeded by the pressing force of the assembly unit on the formed part, whereby this threshold is determined by the sensor. By this means, control is obtained over the coupling and hence heightened securement and enhanced accuracy of its constancy.

It has moreover proved advantageous to arrange the actuator and sensor in series mechanically, though a parallel arrangement of them is also possible. However the series arrangement brings the advantage that the same coupling conditions are given for both. It is of secondary importance whether in a coaxial arrangement of the sensor and the actuator, the sensor or the actuator is nearer to the formed part.

As the sensor and actuator must satisfy different requirements—for example a relatively long movement is demanded from the actuator under excitation—it is advantageous for the sensor and the actuator to be under different preload forces. Thus, a separately preloaded sensor may additionally sustain the preload for the actuator.

Force sensors are preferred for this purpose, though other sensors may be used too, such as accelerometers or sound emission sensors.

Strong excitation amplitudes, i.e. large vibration movements of the actuator, and relatively strong sensor signals can be obtained if the actuator and sensor consist of piezoceramic disks. Thus, the excitation may be increased additionally if the actuator is a stack element comprising a large number of piezoceramic disks. By employing multilayer technology, such stack elements can be produced having large displacements accompanied by relatively low stressing.

If, however, high accuracy for threshold determination is required, as for triggering the actuator excitation only after a certain pressing force is reached for example, the sensor may be of quartz disks to advantage. Where high accuracy and relatively strong signals are required, a sensor of piezoceramic and quartz disks is a preferred choice.

The design of the actuator/sensor arrangement is made mechanically simple by using actuator and sensor disks of annular shape, which can be assembled in a housing under constant mechanical preload.

Coupling of the actuator/sensor arrangement to the formed part is facilitated by providing the assembly unit with a hand grip for pressing it onto the formed part.

If the coupling element is joined interchangeably to the actuator/sensor arrangement, optimal coupling conditions can be provided for every purpose by varying the coupling elements.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
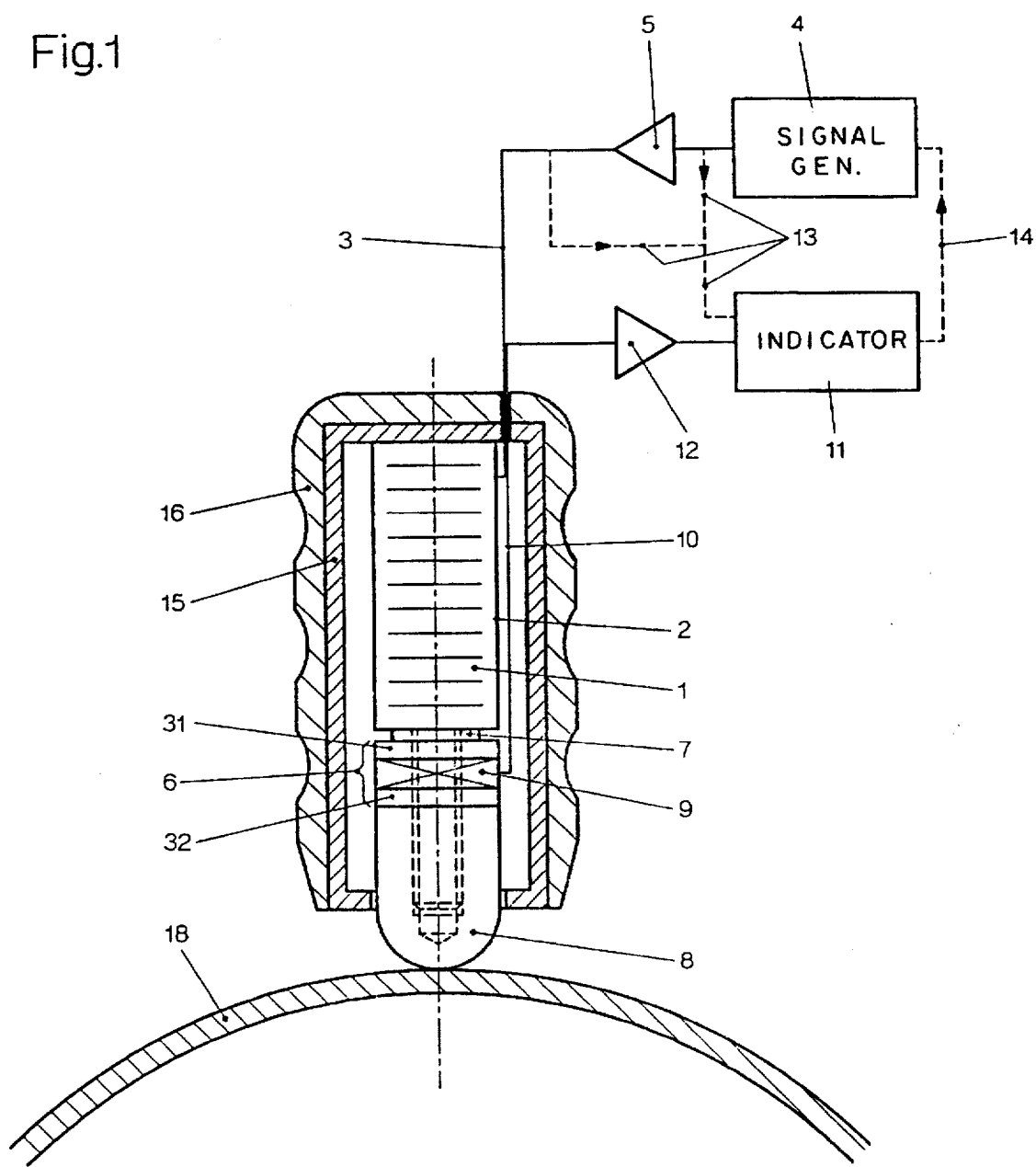
FIG. 1 Schematic representation of the first embodiment of an arrangement according to the invention.

The arrangement according to the invention in FIG. 1 has a first actuator/sensor unit with a number of piezoceramic disks 1 as actuator 2, assembled into a column-like stack element. They are supplied with an excitation voltage via a lead 3 shown schematically.

The excitation voltages are generated by a signal generator 4, which for example may take the form of a pulse or frequency generator. Its signals pass first to a charge amplifier 5 before reaching the actuator 2.

The lower end of the actuator stack element 2, whose disks 1 are preloaded, are joined to a preloaded force measuring element 6, e.g. by threaded element 7. Attached to the force measuring element 6, removably and interchangeably, is a coupling element 8. The force measuring element 6 consists of a upper part 31 and a lower part 32, with a sensor 9 sandwiched between them under preload by threaded element 7, for example. Depending on the coupling conditions required, the coupling element 8 may be of steel for a "hard" coupling for example or of plastic such as Delrin for a "soft" coupling.

In the example shown, the sensor 9 is a an annular disk of piezoceramic. Of course it may also consist of several disks and/or quartz. Via a lead 10, the measuring signals from the sensor 9 are led to a signal indicator 11. Here the signals pass first to a charge amplifier 12 before being displayed after amplification by the indicator 11 and possibly led out for further processing.

To detect the actuator excitation, signals from the generator 4 may be branched off optionally before or after the amplifier 5 and likewise led into the indicator 11 via signal lines 13. If the excitation deviates from the shape or amplitude it ought to have, it is possible to correct the deviations via lines 14.

The actual actuator/sensor unit 2, 6, 8 is surrounded by a preferentially cylindrical basic housing 15, which depending on the application may have an outside hand grip 16 or be mounted in a robot arm, not shown. To test a formed part 18, the unit 2, 6, 8 with its housing 15 is pressed onto the part 18 whose properties are to be established. As already described, the actuator 2 is excited only after a pressing force threshold measured by sensor 9 is exceeded, as indicated for example by the indicator 11 via the line 14.

Figure 2:
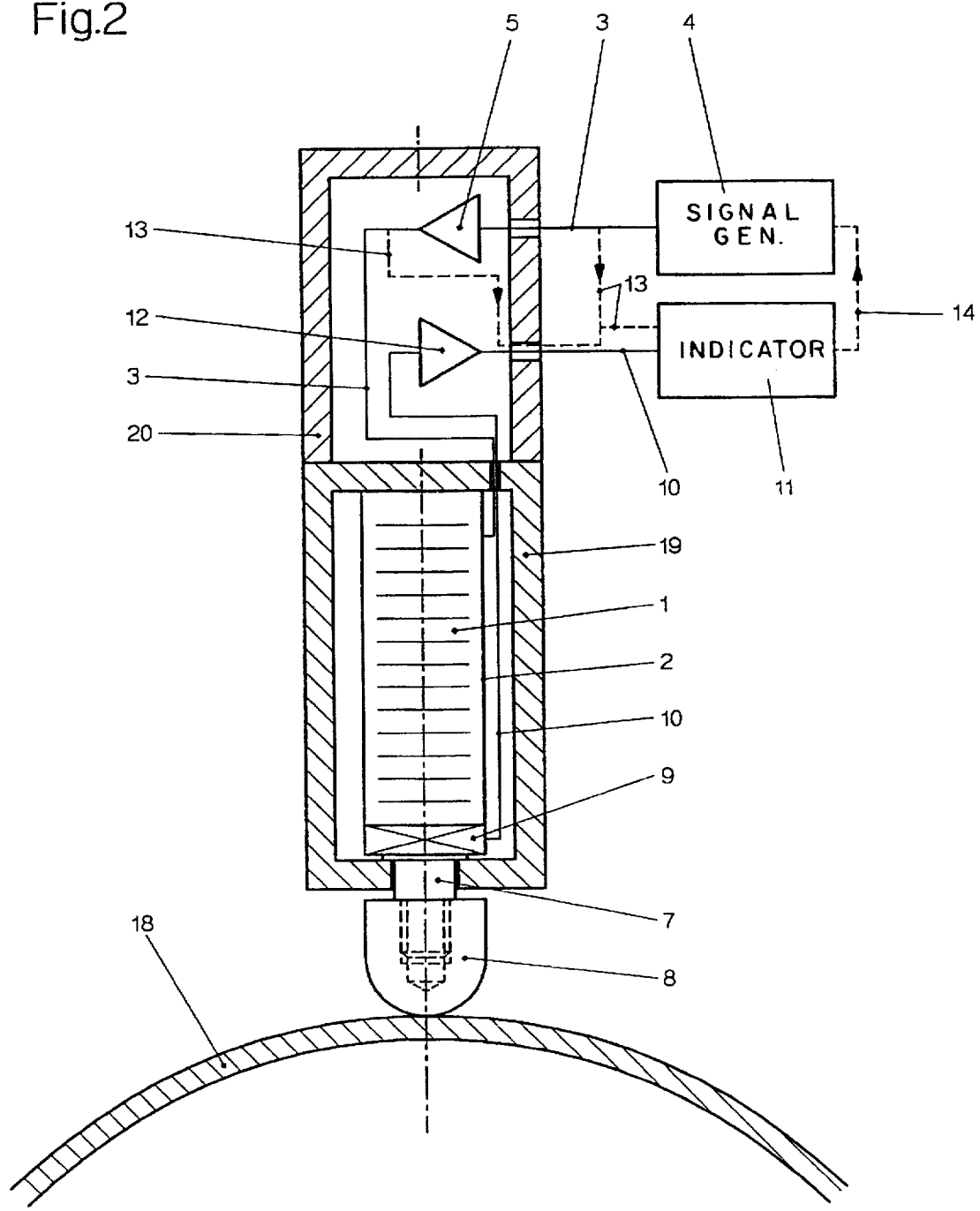
FIG. 2 Variant of the arrangement of FIG. 1 represented similarly.

The arrangement according to FIG. 2 differs from the foregoing example of FIG. 1 only in details. FIG. 2 has the sensor 9 placed not in a separate force measuring element but as one or more disks integrated in the stack element of the actuator 2. Also the amplifiers 5 and 12 are accommodated in the basic housing of the unit 2, 6, 8, which is therefore divided into two part housings 19 and 20. Finally the hand grip 16 is omitted, so that the basic housing 19, 20 in the form shown may be mounted on a robot, not shown.

In both of the actuator/sensor units 2, 6, 8 shown previously in FIGS. 1 and 2, the actuator 2 and sensor 9 are arranged mechanically in series, whereby it is of secondary importance whether the actuator 2 or the sensor 9 is nearer to the formed part 18.

Figure 3:
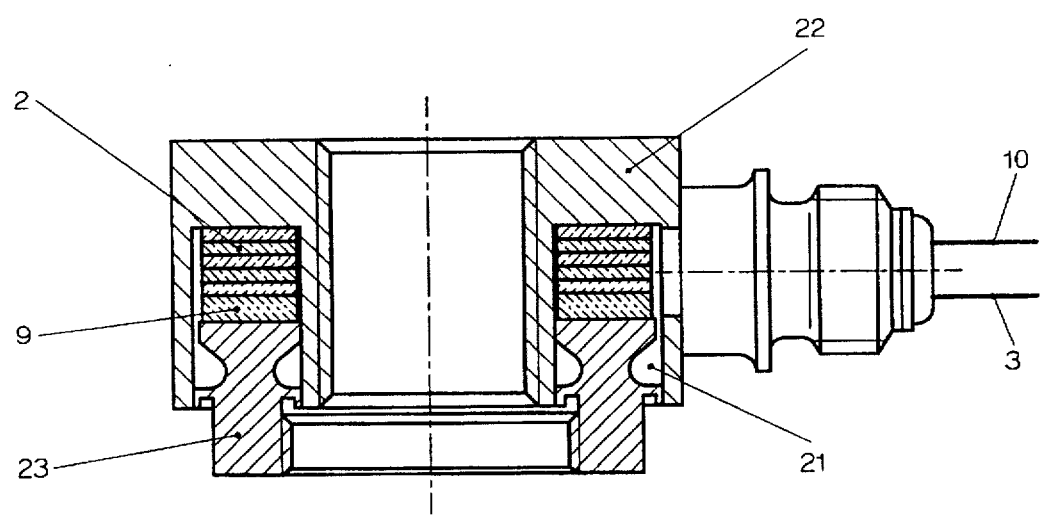
FIG. 3 Another example of an actuator/sensor unit.

The series arrangement has been adopted for the design in FIG. 3 also, where the actuator 2 and sensor 9 are placed in the annular space 21 of a cup-like housing 22 with inside thread. The annular space 21 is open to the bottom and sealed off by a preloading element 23, likewise annular and threaded to housing 22. This preloading element 23 has an inside thread for fitting a coupling element not shown. By means of a screw passing through the inside thread of the housing 22, the unit 2, 9, 22, 23 may be mounted at the top of a holding device, not shown, and pressed onto the formed part 18 via a coupling element.

Figure 4:
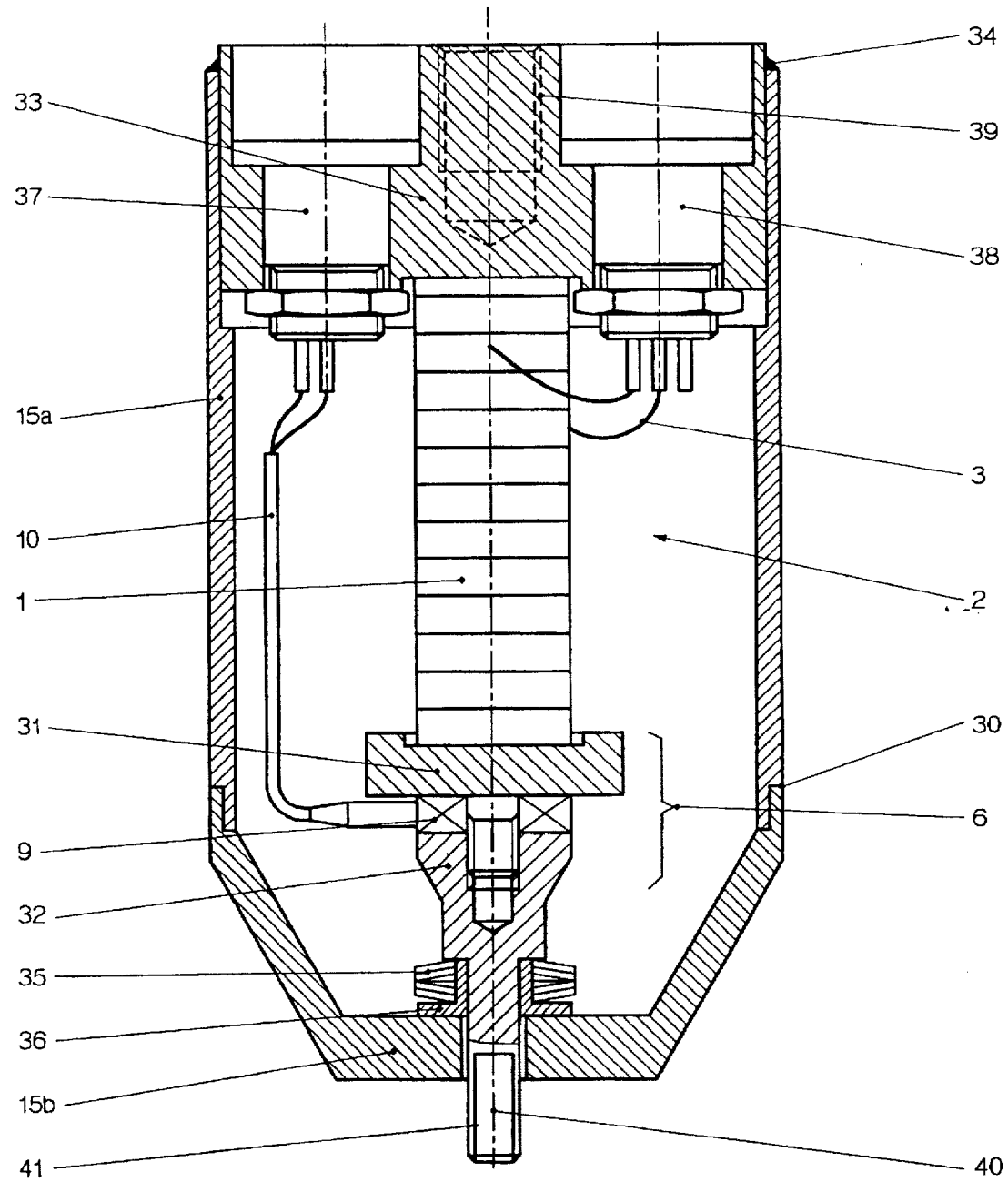
FIG. 4 Design embodiment of an actuator/sensor unit.

In the design according to FIG. 4, the sensor 9 of the measuring element 6 and the actuator 2 are under different preloads. Actuator 2 and sensor 9 are arranged together in the tubular housing 15, which is divided into two parts 15a and 15b welded together at 30 to facilitate assembling.

The sensor 9 of the measuring element 6 is gripped between a preloading screw 31 and a preloading nut 32. It is under a higher preload than the stack of piezodisks 1 of the actuator 2, whose disks are gripped between the preloading screw 31 of the measuring element 6 and a connecting part 33 and are glued to these elements in addition.

The preloading of the piezodisk stack 1 is applied by one or more disk springs 35, which in turn are held by a seal 36 in the housing part 15b. In this embodiment the preload of the disk springs 35 is added to the separate preload of the sensor.

The force of the disk spring 35 acts against the welded joint 34 between the housing part 15a and connecting part 33. The connecting part 33 accommodates the electrical and mechanical connections of the actuator/sensor unit. The connecting part 33 is therefore provided with two sockets 37 and 38 having different numbers of poles and an internal screw thread 39.

The preloading nut 32 of the measuring element 6 has an extension pin 40, which passes through the housing part 15b and has an outside thread 41, on which interchangeable coupling elements 8 may be screwed (FIG. 1).

In comparative testing procedures for the properties of formed parts making use of their dynamic behaviour under acoustic vibrations, the arrangement according to the invention ensures first a constant excitation of the piezoelectric actuator 2 for the acoustic vibrations, and second a constant pressing force when coupling the device to the test object. Thus, changes in the vibration spectrum of the vibrations induced in the test object, which are recorded by the electromechanical sensor 9 integrated in the arrangement, can be ascribed unequivocally to the material of the formed part under test and its altered properties.

What is claimed is:

1. An arrangement for testing the material of formed parts in order to detect material defects and/or properties, whereby the frequency spectrum of mechanical excitation vibrations of a formed part to be tested are compared with the frequency spectrum of a similar formed part having known properties as reference spectrum, the arrangement comprising:

a piezoelectric actuator, an electromechanical sensor and a coupling element, which are combined into one assembly unit;

a signal generator supplying individual pulses or vibrations of variable frequency within a certain range and of constant shape and amplitude to and exciting the actuator;

means of detecting the shape and amplitude of the actuator excitation;

an electronic charge amplifier with an indicator detecting at least the mechanical excitation vibrations of the actuator measured by the sensor; and means for exciting the actuator only after a threshold is exceeded by the pressing force of the assembly unit on the formed part, whereby the pressing force is determined by the sensor.

2. An arrangement according to claim 1, wherein the actuator and the sensor are arranged in series mechanically.

3. An arrangement according to claim 1, wherein the sensor is a force sensor.

4. An arrangement according to claim 1, wherein the actuator and the sensor include piezoceramic disks.

5. An arrangement according to claim 1, wherein the sensor includes piezoceramic and quartz crystal disks.

6. An arrangement according to claim 4, wherein the actuator is a stack element comprising a plurality of piezoceramic disks.

7. An arrangement according to claim 4 wherein the actuator and sensor disks are annular in shape.

8. An arrangement according to claim 1, wherein the assembly unit includes a hand grip for pressing the assembly unit onto the formed part.

9. An arrangement according to claim 1, wherein the coupling element is interchangeable.

10. An arrangement according to claim 1, wherein the sensor and actuator are under different preload forces.

11. An arrangement according to claim 10, wherein the sensor, which is separately preloaded, sustains additionally the preload force for the actuator.

12. An arrangement according to claim 1, wherein the actuator and the sensor are arranged in series mechanically.

13. An arrangement according to claim 1, wherein the sensor is a force sensor.

14. An arrangement according to claim 1, wherein the detecting means is also connected to said indicator.

15. An arrangement for testing the material of formed parts in order to detect material defects and/or properties, whereby the frequency spectrum of mechanical excitation vibrations of a formed part to be tested are compared with the frequency spectrum of a similar formed part having known properties as reference spectrum, the arrangement comprising:

- a piezoelectric actuator, an electromechanical sensor and a coupling element, which are combined into one assembly unit;
- the sensor and actuator being under different preload forces;
- a signal generator supplying individual pulses or vibrations of variable frequency within a certain range and of constant shape and amplitude to and exciting the actuator;
- means of detecting the shape and amplitude of the actuator excitation;
- an electronic charge amplifier with an indicator detecting at least the mechanical excitation vibrations of the actuator measured by the sensor; and 16. An arrangement according to claim 15, wherein the separately preloaded sensor sustains additionally the preload force for the actuator.

* * * * *